United States Patent [19]

Ohta et al.

[11] 4,450,428

[45] May 22, 1984

[54] GAS DETECTING SENSOR

[75] Inventors: Minoru Ohta; Yutaka Hattori, both of Okazaki; Tomio Kawakami, Nishio; Michitosi Onoda, Toyohashi, all of Japan

[73] Assignee: Nippon Soken, Inc., Nishio, Japan

[21] Appl. No.: 336,402

[22] Filed: Dec. 31, 1981

[30] Foreign Application Priority Data

May 25, 1981 [JP] Japan ................... 56-79708

[51] Int. Cl.³ .............................................. H01L 7/00
[52] U.S. Cl. ..................... 338/34; 73/27 R; 422/98
[58] Field of Search ................ 338/34, 35, 28; 73/27 R; 422/58

[56] References Cited

U.S. PATENT DOCUMENTS

| | | | |
|---|---|---|---|
| 3,901,067 | 8/1975 | Boardman, Jr. et al. | 338/34 |
| 3,933,028 | 1/1976 | Laud et al. | 338/34 X |
| 4,007,435 | 2/1977 | Tien | 338/34 |
| 4,012,709 | 3/1977 | Logothetis et al. | 338/34 |
| 4,320,378 | 3/1982 | Taniguchi et al. | 338/34 |
| 4,338,281 | 7/1982 | Treitinger et al. | 422/28 |

*Primary Examiner*—C. L. Albritton
*Attorney, Agent, or Firm*—Cushman, Darby & Cushman

[57] ABSTRACT

A compact and high sensitive gas detecting sensor for detecting the partial pressure of oxygen gas in the exhaust gases of an internal combustion engine is disclosed. The sensor is provided with a sensing element made of the ceramic material having an electrical characteristic which varies in response to variations in the partial pressure of oxygen gas, such as CoO, a base member made of ceramic material having a characteristic of generating heat when an electric current is supplied thereto, such as silicon carbide. The sensing element is integrally fixed to the base member through an insulating layer made of ceramic material. To the base member, electrodes are connected for supplying an electric current thereto so that the base member is maintained at a predetermined temperature regardless of the temperature change of the exhaust gases.

11 Claims, 20 Drawing Figures

GAS DETECTING SENSOR

BACKGROUND OF THE INVENTION

The present invention relates to a gas detecting sensor for detecting the partial pressure of oxygen gas contained within exhaust gases discharged from an internal combustion engine and measuring air/fuel ratio of the combustion mixture to be supplied into the internal combustion engine.

Recently, "lean burn system" that is, the system of operating an internal combustion engine with an air/fuel ratio larger than the stoichiometric value thereof, is proposed and employed in practice in order to reduce harmful components contained within the exhaust gases and lower the fuel consumption.

The above described "lean burn system" requires a detecting means for accurately detecting air/fuel ratio in a range of lean mixtures.

U.S. Pat. Nos. 3,933,028 and 4,012,709 show examples of such a detecting sensor as described above.

These detecting sensors are provided with a sensing element made of cobalt monoxide (CoO) or an alloy of cobalt monoxide (CoO) and magnesium oxide (MgO). These detecting sensors are further provided with a heating means for heating and maintaining the sensing element at a predetermined temperature, for example 900° C. in order to prevent cobalt monoxide from changing into tricobalt tetroxide ($Co_3O_4$) and to compensate output fluctuation caused by the temperature change.

These conventional detecting sensors have problems as follows.

Since the heating coil is used for heating the sensing element, the structure of the sensor becomes complex and it is troublesome to mount the sensor to the exhaust pipe.

Since the sensing element is formed into a cylindrical or disc-shaped block and the heating coil is arranged around the housing which supports the sensing element, the device becomes large.

Since the sensing element is thick, the sensing element does not exhibit excellent responsive characteristic to the change of the partial pressure of oxygen gas.

Since the sensing element which is supported within the housing, is not directly contacted with the heating coil which is arranged around the housing, high heating efficiency is not obtained so that it takes a while for heating the sensing element to a predetermined temperature and that the consumption of electric power becomes large.

Accordingly, one object of the present invention is to provide a compact gas detecting sensor having simple construction of which sensing element exhibits excellent responsive characteristic.

Another object of the present invention is to provide an improved gas detecting sensor which can be produced with high working efficiency.

DESCRIPTION OF THE DRAWINGS

Other objects and advantages of the invention will become apparent from the follwing description of embodiments with reference to the accompanying drawings wherein.

SUMMARY OF THE INVENTION

The gas detecting sensor of the present invention is provided with a base member which also operates as a heating means, electrodes formed on the base member and a sensing element formed on the base member so as to be contacted with the electrodes. The base member is made of ceramic material which generates heat when an electric current is supplied thereto.

According to the present invention, since the base member on which the sensing element is formed, also operates as the heating means, the structure of the sensor can be made simple and the size thereof can be made small.

Since the sensing element is formed like a film, the sensing element exhibits excellent responsive characteristic.

And since the sensing element is formed on the base member which also operates as a heating means, heating efficiency can be made high.

Furthermore, according to the present invention, a gas detecting sensor can be easily produced by printing the materials for the electrodes and the sensing element on the surface of the ceramic base member and sintering together.

DETAILED DESCRIPTION OF THE INVENTION

Hereinafter, the present invention will be explained in detail in accordance with several embodiments with reference to the accompanying drawings.

Figure 1:
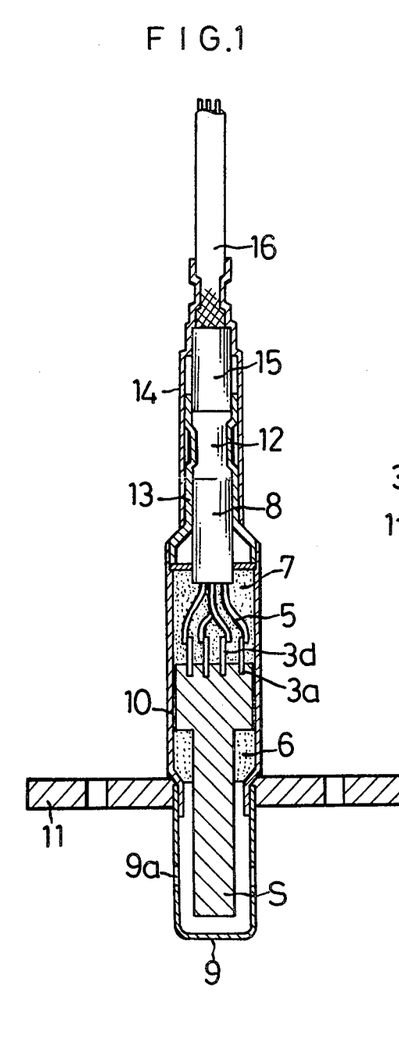
FIG. 1 is a sectional veiw of a gas detecting device wherein a gas detecting sensor of the present invention is accomodated.
Figure 2:
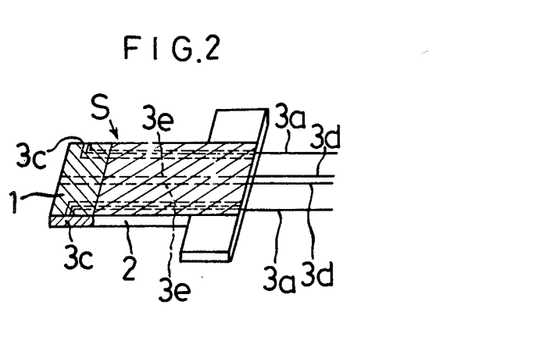
FIG. 2 is a perspective view of the sensor of a first embodiment.

FIG. 1 and FIG. 2 show a first embodiment of the present invention.

In the first embodiment, the gas detecting sensor S comprises a plate shaped base body 2, one pair of electrodes 3c which are continuously formed along both side edges of the upper surface of the base body 2 and on both side surfaces of the top end portion thereof for supplying electric current to the base body 2, a film shaped sensing element 1 which is formed on the top end portion of the surface of the base body 2 so as to be electrically insulated therefrom, another pair of electrodes 3e which are formed on the surface of the base body 2 so as to be electrically insulated therefrom, one end of which is connected to the sensing element 1, respectively, lead wires 3a and 3d which are connected to the electrodes 3c and 3e, respectively, and an insulating layer covering the electrodes 3e.

The base body 2 is made of ceramic material which generates heat when an electric current is supplied thereto, such as silicon carbide, lanthanchromite, silicon nitride and titanium carbide.

The sensing element 1 is made of ceramic material of which electric resistance changes in accordance with the change of the partial pressure of oxygen gas, such as cobalt monoxide, titanium oxide, nickel monoxide, zirconium oxide, tin oxide and zinc oxide.

The electrodes $3c$ and $3e$ are made of platinum, platinumrhodium alloy or the like.

The insulating layer is made of alumina, spinel, mullite or the like.

The base body 2 is accomodated within a protecting cover member 9 made of heat resistant metal and provided with holes $9a$ for introducing exhaust gases therein, and a pipe member 10 connected to the cover member 9. In the connecting portion of the protecting cover member 9 and the pipe member 10, a flange member 11 for fixing the cover member 9 and the pipe member 10 to an exhaust pipe (not shown) is mounted.

The sensor S is supported by a retaining member 6 made of a sintered body such as alumina within the pipe member 10. And to the base end portion of the base body 2, the lead wires $3a$ and $3d$ and the sub lead wires 5 which are connected to the lead wires $3a$ and $3d$ are fixed within the pipe member 10 by means of inorganic binding agent 7.

To the pipe member 10, pipe members 13 and 14 are connected in order. Within the pipe members 13 and 14, an insulating pipe 8 made of alumina or the like, a bush 12 made of fluorine-contained rubber or the like and a heat resistant rubber member 15 made of silicon rubber or the like are accomodated and the sub-lead wires 5 are inserted therethrough and extends outside the pipe member 14 with being covered by a covered member 16.

Hereinafter, the structure of the detecting sensor S of the present invention will be explained together with the producing steps thereof with reference to FIGS. 3 to 6.

Figure 3A:
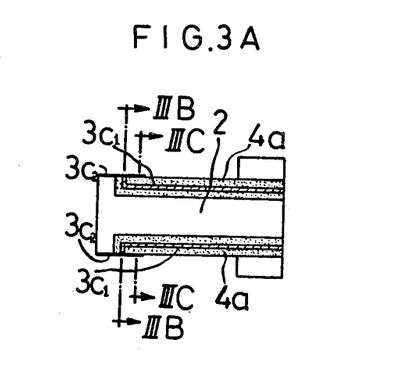
FIG. 3 to FIG. 6 are views showing the process of producing the sensor of a first embodiment.
Figure 3B:
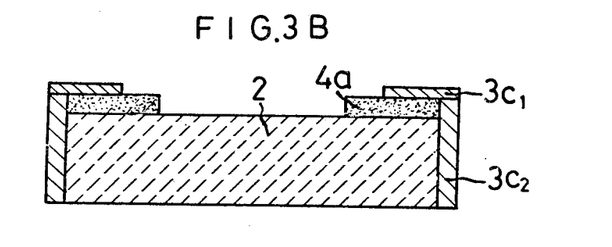
Figure 3C:
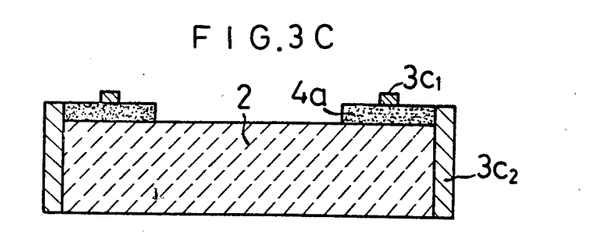

As shown in FIGS. 3A, 3B and 3C, on the upper surface of the sintered ceramic base plate 2, insulating layers $4a$ made of alumina paste or the like are printed along both side edges thereof so as to extend in the longitudinal direction thereof and dried. Then, one portion $3c_1$ of each electrode $3c$ is printed on each insulating layer $4a$. And on each side surface of the top end portion of the base plate 2, the other portion $3c_2$ of each electrode $3c$ is printed so as to continue from one portion $3c_1$ of each electrode $3c$.

Figure 4A:
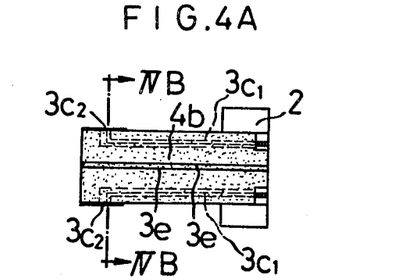
Figure 4B:
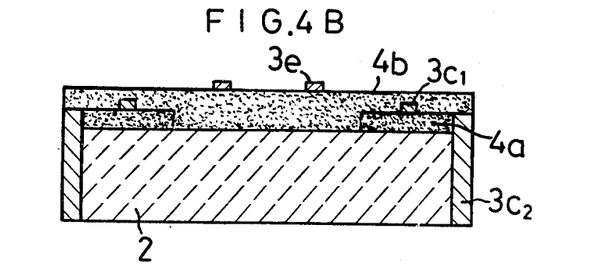

Next, as shown in FIGS. 4A and 4B, on the whole surface of the base plate 2, on which one electrode portion $3c_2$ are formed, an insulating layer $4b$ made of alumina paste or the like is printed except for the base end portion (righthand portion in FIG. 4A) of each of one electrode portion $3c_1$.

After the insulating layer $4b$ is dried, a pair of electrodes $3e$ are printed in the central portion of the surface of the insulating layer $4b$. Then, the obtained base plate on which the insulating layers and the electrodes are printed is sintered at 1500° to 1600° C. for about 5 hours.

Figure 5A:
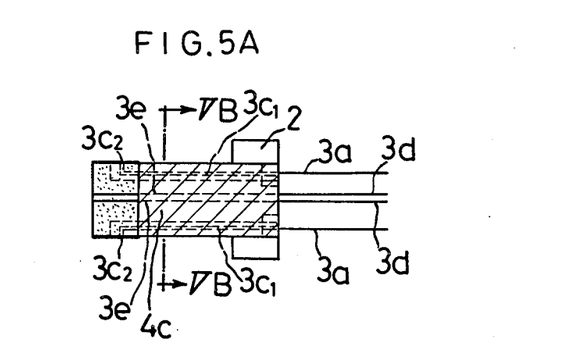
Figure 5B:
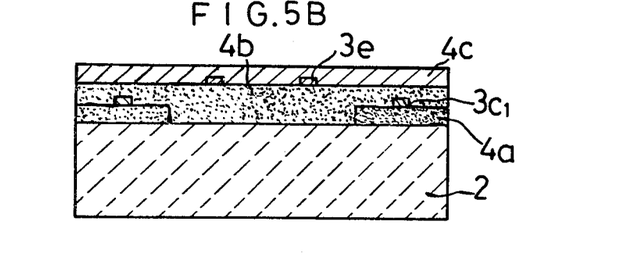

Then, as shown in FIGS. 5A and 5B, the vase end portion of each of the electrodes $3c_1$ and $3e$ is coated with nickel and lead wires $3a$ and $3d$ are copper-soldered thereto, respectively. And the surface of the base plate 2 except for the top end portion thereof is covered with electric insulating material such as the paste of glass matter so as to completely cover the electrodes $3c_1$ and $3e$ to form a protecting layer $4c$.

Figure 6A:
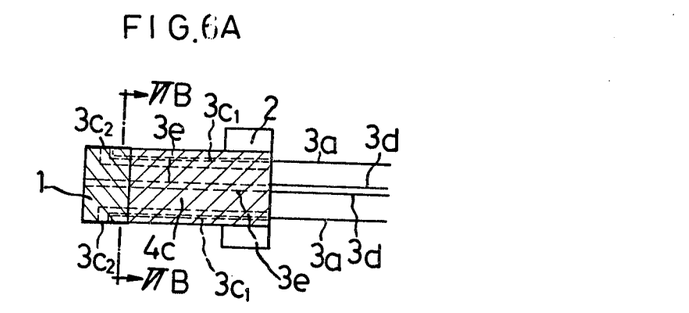
Figure 6B:
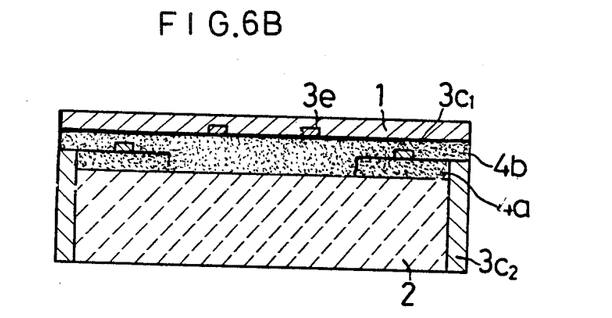

Next, as shown in FIGS. 6A and 6B, on the surface of the top end portion of the base plate 2 on which the protecting layer $4c$ is not formed, paste like cobalt monoxide (CoO) is printed so as to cover the end of each of the electrodes $3e$ and sintered at 800° C. for about 1 hour to form a sensing element 1.

In FIGS. 3B, 4B, 5B and 6B, each of the electrodes $3c_1$, $3c_2$, and $3e$ and the insulating layers $4a$, $4b$ and $4c$ is drawn thicker than the actual thickness thereof in order to clarify the structure thereof.

In the detecting sensor produced by the above described producing steps, the base plate 2 which supports the sensing element 1 also operates as the heating means. When the electric current is supplied to the base plate 2 through the lead wires $3a$ and the electrodes $3c_1$, the temperature of the top end portion of the base plate 2 to which the sensing element 1 is fixed, rapidly rises so that large electric consumption is not required for heating the sensing element 1.

Since the sensing element 1 is formed into a thin film, the exhaust gases diffuse within the sensing element 1 for a very short time so that excellent responsive characteristic can be obtained.

Furthermore, since the electrodes $3c_1$ and $3e$ which are fixed to the upper surface of the base plate 2 are completely covered with the protecting layer $4c$ and the sensing element 1, short circuit which would occur between the electrodes $3c$ and $3e$ when electric-conductive substance such as carbon contained within the exhaust gases is accumulated therebetween, can be prevented.

The electrodes for supplying an electric current to the base body can be modified into various forms due to the resistance value of the base body, electric power, heating temperature, etc.

Figure 7:
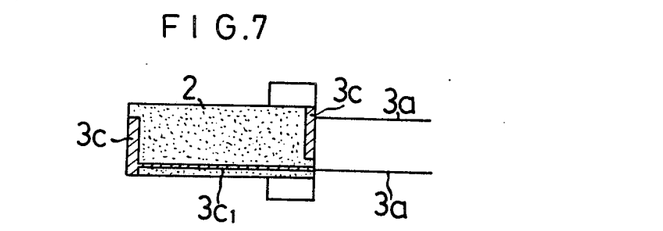
FIG. 7 to FIG. 9 are views showing the arrangement of electrodes and lead wires in sensors of a second to a fourth embodiments of the present invention, respectively.

In the second embodiment shown in FIG. 7, electrodes $3c$ are formed in nearly whole width of each of the top and base ends of the base plate 2. One of the electrodes $3c$ is connected to one of lead wires $3a$ through a longitudinally extending portion $3c_1$ thereof which is formed along one of the side edges of the base plate 2 while the other electrode $3c$ is connected to the other lead wire $3a$. In the gas detecting sensor of the second embodiment, the whole of the base plate 2 is heated.

Figure 8:
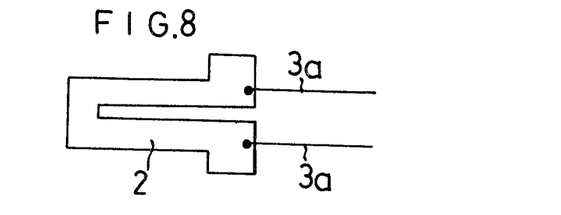

In the third embodiment shown in FIG. 8, the base plate 2 is formed into a U-shape and lead wires $3a$ are connected to two base ends of the base plate 2. The gas detecting sensor of the third embodiment provided with the U-shaped base plate 2 does not require such insulating layers $4a$ as shown in FIG. 3.

Figure 9:
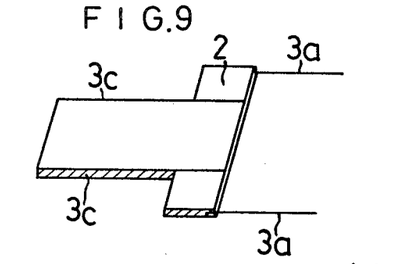

In The fourth embodiment shown in FIG. 9, on the whole of the side surfaces of the base plate 2, electrodes $3c$ are formed and a lead wire $3a$ is connected to each end of the electrodes $3c$.

FIGS. 10 to 13 show a fifth embodiment of the present invention. The structure of the gas detecting sensor of the fifth embodiment will be explained together with the producing method thereof.

A pair of semi-columnar base bodies $2a$ and $2b$ are made of ceramic material which generates heat by supplying electric current thereto.

Figure 10:
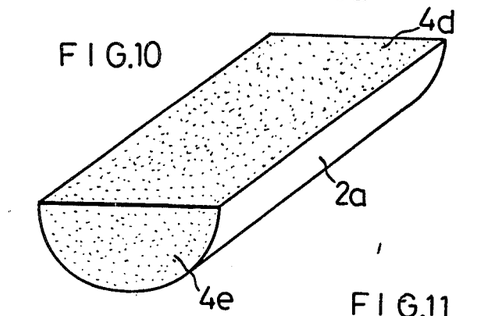
FIG. 10 to FIG. 13 are views showing the steps for producing a sensor of a fifth embodiment.

As shown in FIG. 10, on the flat surface and one semicircular end surface of the base body $2a$, insulating layers $4d$ and $4e$ are printed.

Figure 11:
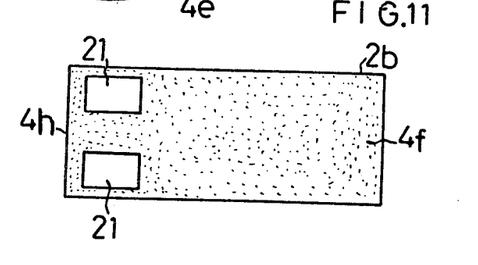

And as shown in FIG. 11, on the flat surface of the base body $2b$, an insulating layer $4f$ is printed except for rectangular portions 21 whcih are formed in both sides of one end portion thereof. And also on one semicircular end surface of the base body $2b$, an insulating layer $4h$ is printed.

Figure 12:
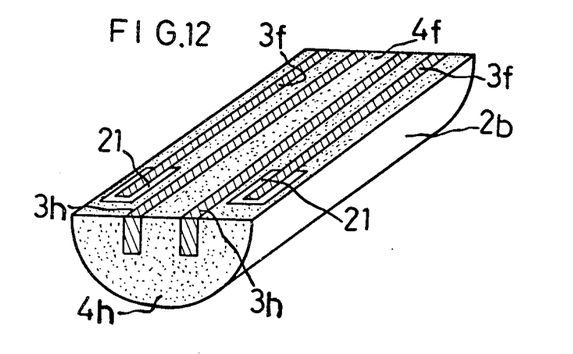

Next, as shown in FIG. 12, on the flat surface of the base body 2b, electrodes 3f are printed along the side edges thereof. One end of each electrode 3f is located in each rectangular portion 21 and is printed on the base body 2 directly. And on the flat surface of the base body 2b, a pair of electrodes 3h are printed between the electrodes 3f, so as to extend on the side surface of the base body 2b on which the insulating layer 4h is formed. Then, the obtained base body 2b is sintered at 1500° C. to 1600° C. for about 5 hours.

Figure 13:
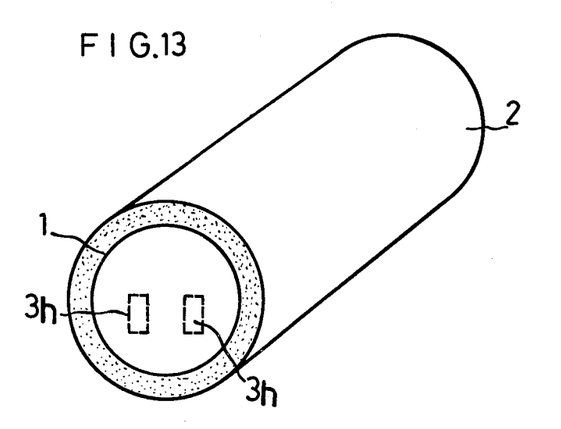

Next, as shown in FIG. 13, on the flat surface of the base body 2b, the flat surface of the base body 2a is laid and the base bodies 2a and 2b are heated under pressure to form a columnar structure 2. At this time, the electrodes 3f and 3h are connected to lead wires (not shown), respectively.

At last, on one end surface of the structure 2 on which the electrodes 3h are formed, paste of cobalt monoxide is printed and sintered at about 800° C. for about 1 hour to form a sensing element 1.

Figure 14:
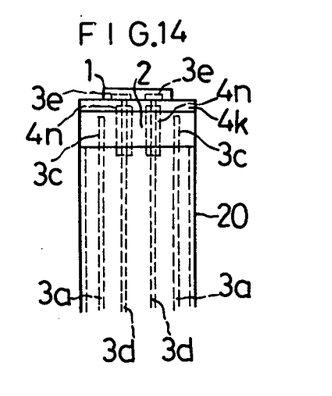
FIG. 14 is a plane view of a sensor of a sixth embodiment.
Figure 15:
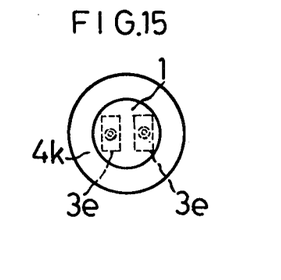
FIG. 15 is an end view of the sensor of the sixth embodiment.

FIGS. 14 and 15 show a sixth embodiment of the present invention. To the top end of a cylindrical supporting member 20, a disc-shaped base body 2 made of ceramic material which generates heat when electric current is supplied thereto, is adhered. On the surface of the base body 2, an insulating layer 4k is formed and on the surface of the insulating layer 4k, a sensing element 1 is formed. Within the base body 2, a pair of electrodes 3c which are connected to lead wires 3a, respectively are embedded. And also within the base body 2 and the insulating layer 4k, a pair of electrodes 3e are embedded so that one end thereof extends to the sensing element 1. The other end of each of the electrodes 3e is connected to each of lead wires 3d, and the electrodes 3e is covered with an insulating layer 4n within the base body 2.

As described above, according to the present invention, the base member on which the sensing element is fomed, also operates as the heating means so that the structure of the sensor can be made simple and the size thereof can be made small.

Since the sensing element is formed on the base member which also operates as a heating means, like a film, the sensing element exhibits excellent responsive characteristic and high heating efficiency is obtained.

Furthermore, according to the present invention, a gas detecting sensor can be easily produced by printing the materials for the electrodes and the sensing element on the surface of the ceramic base member and sintering together.

Having now fully described the invention, it will be apparent to one of ordinary skill in the art that many changes and modifications can be made thereto without departing from the spirit or scope of the invention as set forth herein.

What is claimed is:

1. A gas detecting sensor for detecting the partial pressure of oxygen gas contained within exhaust gases, comprising:

a base body made of ceramic material having a characteristic of generating heat when an electric current is supplied thereto;

one pair of electrodes which are fixed to said base body at a predetermined interval, one end of each of said one pair of electrodes being directly fixed to said base body so as to form an electric path crossing said base body therebetween while the other portion of each of said one pair of electrodes being fixed to said base body through a first insulating layer;

a sensing element made of ceramic material having electrical characteristic in response to the partial pressure of oxygen gas, which is closely fixed to said base body through a second insulating layer in the vicinity of said electric path;

another pair of electrodes which are fixed to said base body so as to be electrically insulated therefrom and to be contacted with said sensing element for supplying an electric current to said sensing element; and two pairs of lead members, one pair of said lead members being connected to said one pair of electrodes for supplying an electric current to said base body while the other pair of said lead members being connected to said another pair of electrodes for supplying an electric current to said sensing element.

2. A gas detecting sensor according to claim 1, wherein:

said ceramic material of said base body is selected from the group consisting of silicon carbide, lanthanchromite, silicon nitrite and titanium carbide.

3. A gas detecting sensor according to claim 1, wherein:

said ceramic material of said sensing element is selected from the group consisting of cobalt monoxide, titanium oxide, nickel monoxide, zirconium oxide, tin oxide and zinc oxide.

4. A gas detecting sensor according to claim 1, wherein:

said insulating layer is made of ceramic material selected from the group consisting of alumina, spinel and mullite.

5. A gas detecting sensor according to claim 1, wherein:

said electrodes are made of a material selected from the group consisting of platinum and platinum-rhodium alloy.

6. A gas detecting sensor according to claim 1, wherein:

said base body has a columnar shape;

said sensing element is fixed to one end surface of said base body through said insulating layer;

said one pair of electrodes are embedded within said base body so as to be electrically insulated from said sensing element and said another pair of electrodes;

said another pair of electrodes are embedded within said base body so as to be electrically insulated from said base body; and one end of each of another pair of electrodes is contacted with said sensing element.

7. A gas detecting sensor according to claim 1, wherein:

said base body has a plate shape;

said one end of each of said one pair of electrodes is formed on each of both side surfaces of one end portion of said plate-shaped base body; and said sensing element is in the form of a film formed on the upper surface of said one end portion of said plate-shaped base body.

8. A gas detecting sensor according to claim 7, wherein:

said first insulating layer is printed on both side portions of the upper surface of said plate-shaped base body except for said one end portion thereof;

said the other portion of each of said one pair of electrodes are printed on said first insulating layer;

said second insulating layer is printed on the whole upper surface of said plate shaped base body so as to cover said the other portion of each of said one pair of electrodes;

said sensing element and said another pair of electrodes are printed on said second insulating layer; and said base body, said first and second insulating layers, said sensing element and said electrodes are integrally sintered.

9. A gas detecting sensor according to claim 1, wherein:

said base body is composed of a pair of column-shaped blocks, each of which is provided with one flat side surface and end surfaces;

said first insulating layer is printed on the whole of said flat surfaces of said pair of blocks except for two portions of said flat surface of one of said pair of blocks, each of which is positioned at each of sides thereof, said second insulating layer is printed on the whole of said end surfaces of said pair of blocks;

said one end of each of said one pair of electrodes is printed on each of two portions of said flat surface of one of said pair of blocks;

said another pair of electrodes are printed on said first insulating layer of one of said pair of blocks so as to extend on said second insulating layer of one of said pair of blocks;

said pair of blocks are sintered, respectively and combined together by joining said flat surfaces of said blocks; and said sensing element is printed on one end surface of said combined base body through said second insulating layer so as to be contacted with said another pair of electrodes and sintered.

10. A gas detecting sensor according to claim 1, further comprising:

a protecting layer made of insulating material, which covers said another pair of electrodes.

11. A gas detecting sensor according to claim 10, wherein:

said insulating material of said protecting layer is selected from the group consisting of alumina, spinel and mullite.

* * * * *